United States Patent [19]

Fletcher et al.

[11] 4,027,524
[45] June 7, 1977

[54] APPARATUS FOR DETERMINING THERMOPHYSICAL PROPERTIES OF TEST SPECIMENS

[76] Inventors: James C. Fletcher, Administrator of the National Aeronautics and Space Administration, with respect to an invention of Theodore R. Creel, Jr., Yorktown; Robert A. Jones, Newport News, both of Va.; Richard R. Corwin, Xenia; Joseph S. Kramer, Dayton, both of Ohio

[22] Filed: Feb. 27, 1976

[21] Appl. No.: 662,175

[52] U.S. Cl. ............................................. 73/15 R
[51] Int. Cl.² ...................................... G01N 25/18
[58] Field of Search .............. 73/15 R, 15 A, 15 B

[56] References Cited
UNITED STATES PATENTS

| | | | |
|---|---|---|---|
| 3,672,204 | 6/1972 | Green | 73/15 |
| 3,789,654 | 2/1974 | Jones | 73/15 |

OTHER PUBLICATIONS

Katayama et al., "Transient Comparison Methods of Simultaneous Measurement of Thermal Properties" in Bull JSME (Japan), vol. 12, No. 54, 1969, pp. 1439–1447.

*Primary Examiner*—Herbert Goldstein

*Attorney, Agent, or Firm*—Howard J. Osborn; William H. King; John R. Manning

[57] ABSTRACT

Apparatus for directly measuring the quantity $\sqrt{\rho c k}$ of a test specimen such as a wind tunnel model where $\rho$ is the density, $c$ is the specific heat and $k$ is the thermal conductivity of the specimen. The test specimen and a reference specimen are simultaneously subjected to the heat from a heat source. A thermocouple is attached to the reference specimen for producing a first electrical analog signal proportional to the heat rate $\dot{Q}$ that the test specimen is subjected to and an infrared radiometer that is aimed at the test specimen produces a second electrical analog signal proportional to the surface temperature T of the test specimen. An analog-to-digital converter converts the first and second electrical analog signals to digital signals. These digital signals are applied to a computer for determining the quantity $\sqrt{\rho c k}$ by computing the quantity $$\frac{\dot{Q}}{T-T_i} \frac{2}{\sqrt{\pi}} \sqrt{t}$$

where $T_i$ is the initial test specimen temperature and $t$ is the elapsed time from the time that the specimens were first subjected to the heat source.

7 Claims, 1 Drawing Figure

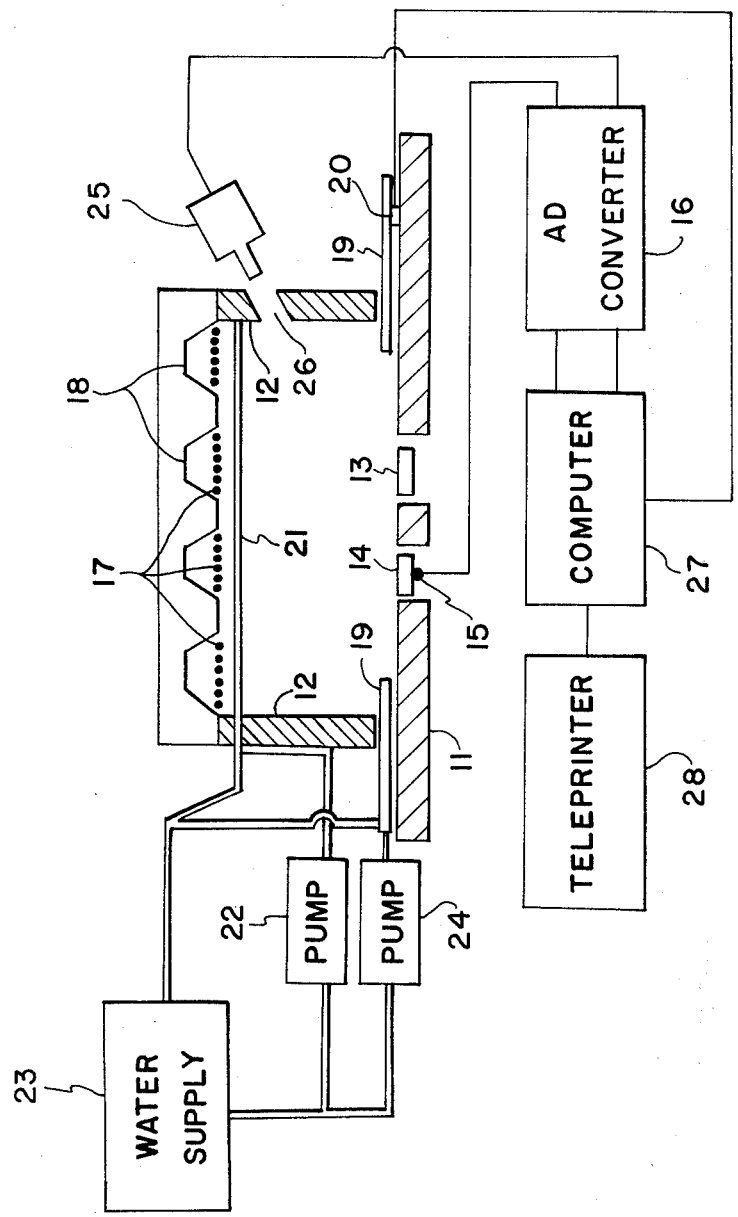

APPARATUS FOR DETERMINING THERMOPHYSICAL PROPERTIES OF TEST SPECIMENS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; rw USC 2457).

BACKGROUND OF THE INVENTION

The invention relates to apparatus for directly measuring the quantity $\sqrt{\rho c k}$ of a test specimen where $\rho$ is the density, $c$ is the specific heat and $k$ is the thermal conductivity of the specimen.

A previous technique for measuring the quantity $\sqrt{\rho c k}$ is disclosed in the U.S. Pat. No. 3,789,654. This previous technique consists of using a model made from a low thermal conductivity material covered with a phase-change coating which is an accurate surface temperature indicator. This indicator called "Tempilaq" consists of wax crystals which melt at a prescribed melting temperature. If the model is heated, the coating will melt when the surface reaches a calibrated phase-change temperature. Knowing this melt temperature, the time to reach the melt temperature from the initial temperature, and the heating rate, the combination of thermophysical properties $\sqrt{\rho c k}$ is determined from the equation:

$$\sqrt{\rho c k} = \frac{\dot{Q}}{T - T_i} \frac{2}{\sqrt{\pi}} \sqrt{t} \quad (1)$$

where $\dot{Q}$ is the imposed heating rate, $T_i$ is the initial model temperature prior to heating, $T$ is the melting temperature and $t$ is the elapsed time from the onset of heating until melting occurs.

In this prior technique a camera was used to record the sample surface temperature as indicated by the melting of the phase-change coating. Some of the disadvantages of this technique are that the camera may not photograph the sample at the exact time the phase-change coating melts; the exact time of phase transition is often difficult to interpret visually; the sample and calorimeter must be taken out of the apparatus in order to be coated with the phase-change coating; and the results may not be known for several days because of delays in photoprocessing and strip chart reading.

It is the primary purpose of this invention to provide apparatus for directly measuring the quantity $\sqrt{\rho c k}$ of a test specimen that eliminates disadvantages encountered in the measuring technique disclosed in U.S. Pat. No. 2,789,654.

SUMMARY OF THE INVENTION

In the present invention a test specimen such as a model and a reference specimen are simultaneously subjected to the heat from a heat source. A thermocouple is attached to the reference specimen for producing a first analog signal proportional to heating rate $\dot{Q}$. An infrared radiometer aimed at the surface of the test specimen produces a second analog signal proportional to surface temperature T. A water-cooled shutter is used to simultaneously subject the specimens to the heat source. A microswitch on the underneath side of the shutter is tripped at the instant the heat source is applied to the specimens. The two analog signals are converted to digital signals by means of an analog-to-digital converter and applied to a computer along with a signal from the microswitch. The computer then calculates the quantity $\sqrt{\rho c k}$ in accordance with equation (1). A water filter is located between the heat source and the specimens to absorb all wavelengths larger than about 1.8 microns.

BRIEF DESCRIPTION OF THE DRAWING

The sole FIGURE in this application is a combination schematic block diagram of the embodiment of the invention selected for illustration.

DETAILED DESCRIPTION OF THE INVENTION

Turning now to the embodiment of the invention selected for illustration in the drawing, the numeral 11 designates a sample holder having sidewalls 12. A test specimen 13 and a reference specimen 14 are located within the sample holder 11. Reference specimen 14 is made from copper and has a thermocouple 15 attached to it on its lower side for producing an analog signal proportional to the change in temperature $\dot{Q}$ of the reference specimen 14. This analog signal is applied to an analog-to-digital converter 16. A plurality of tungsten filament lamps 17 with reflectors 18 are mounted inside the sample holder to provide a radiant heat source having a temperature of 5000° F. A water-cooled shutter 19 is mounted in sample holder 11 so that it can be inserted or removed from between the heat source and the specimens. A microswitch 20 is located underneath the shutter and is tripped just as the shutter passes over the region of specimen 13.

An infrared radiometer 25 is aimed onto the surface of the test specimen 13 through an opening 26 in the walls of the sample holder for producing an analog signal proportional to the surface temperature of test specimen 13. Infrared radiometers for providing this function are commercially available and can be, for example, a model IT-7A infrared thermometer, manufactured by Barnes Engineering Company. The output voltage swing for this device, from 0 to 5 volts, spans the temperature range of 50° to 500° F. The infrared thermometer lens has a field-of-view of 0.7° which will measure the temperature over a 0.4-inch target spot at a distance of 20 inches. Aiming and focusing of the radiometer onto the area of interest is accomplished by in-line through-the-lens viewing. By focusing the objective lens, a reticle in the eyepiece indicates to the observer the precise region of the specimen where temperature is to be measured. The output of radiometer 25 is applied to analog-to-digital converter 16.

Since the radiant heat source will be at a temperature of 5000° F., it will emit a considerable amount of radiation over the passband of the infrared radiometer. The envelopes of the heating lamps are made of high temperature quartz which consist almost entirely of silica. These materials absorb much of the radiation at wavelengths larger than 5 microns.

The absorbed radiation will raise the quartz envelope temperature considerably higher than the lowest temperature to be measured by the radiometer. The quartz envelopes will then reradiate at relatively long wavelengths extending over the passband of the radiometer. Although the reflectance of the target specimens are small (less than 5%) at these wavelengths and both the quartz envelopes and the target specimens are diffuse radiators and reflectors, this reradiated energy nevertheless can represent a significant noise source to the radiometer.

To eliminate this noise source a water absorption filter 21 is mounted just above the shutter 19 between the specimens and the heating lamps 17. Water filter 21 consists of two parallel glass plates with water flowing between them. The water will absorb all wavelengths larger than about 1.8 microns including radiation within the spectral passband of the radiometer. The water to filter 21 is supplied by a pump 22 from a water supply 23. The water to shutter 19 is supplied by a pump 24 from water supply 23.

The two analog signals applied to analog-to-digital converter 16 are converted to digital signals which are applied to digital computer 27 that computes the quantity $\sqrt{\rho c k}$ in accordance with equation (1). After computation of the heating rate, sample temperature, elapsed time and the quantity $\sqrt{\rho c k}$ are printed by a teleprinter 28.

There are many analog-to-digital converters and computers which will perform the function provided for by analog-to-digital converter 16 and computer 17. One such analog-to-digital converter is the Adacus II-S manufactured by Sun Systems, Inc., and one such computer is Hewlett Packard Model 2100A computer, two Model 12566A Duplex Registers, and one Model 2752 Buffered Teleprinter Input-Output with 12531b Interface Kit. The 2100A is a general digital computer with 4096 words of core memory designed for a wide range of small computer applications. In this application it provides intermediate storage for the digitized temperature and heating rate data, as well as the corresponding time word; means for linearizing the inherently nonlinear output of the infrared thermometer; scaling of both signals in terms of degrees F and Btu/ft²/sec for the computation of $\sqrt{\rho c k}$; and the control and formatting so that temperature versus time, heating rate versus time and $\sqrt{\rho c k}$ versus time can be listed on the teletype.

The 12566A Duplex Registers provide the required circuitry for interfacing the Two Channel Data System with the computer.

The 2752 Buffered Teleprinter Input/Output provides the means for operator communication with the computer. This communication can take the form of commands or instructions entered through the keyboard or paper tape reader by the operator, or printed output from the computer to the operator.

In the operation of this invention with the shutter 19 closed and water passing through the shutter, the lamps 17 are turned on and the radiometer 25 is aimed in the direction of specimen 13. The shutter is then opened which trips microswitch 20 sending a signal to the computer telling it that the computing time is to start. This signal telling the computer that the computing time is to start could be supplied by other means such as a manually operated switch. The thermocouple 15 then produces an analog signal proportional to the rate of change of the temperature of reference specimen 14. Infrared radiometer 26 produces a signal proportional to the surface temperature of test specimen 13. These two analog signals are converted to digital signals by means of analog-to-digital converter 16 and applied to computer 27 which computes the quantity $\sqrt{\rho c k}$ in accordance with equation (1). The quantities $\sqrt{\rho c k}$, heating rate, sample temperature and elapsed time are then printed out by teleprinter 28.

The advantage of this invention is that the quantity $\sqrt{\rho c k}$ is measured directly on the specimen or model under transient conditions consistent with those experienced by the model in a wind tunnel. Just as important is the fact that thermophysical property data can be determined quickly and easily, expediting the analysis of wind tunnel results. (Seven minutes from initiation of the test, $\sqrt{\rho c k}$ is printed by the teleprinter). Also, the sample and calorimeter are not removed from the apparatus between tests, thus different heating rate tests may be applied with little waiting time between tests. In addition, $\sqrt{\rho c k}$ data are obtained for a number of different surface temperatures from a single test whereas with the previous method one test was required for each sample surface temperature of interest.

What is claimed is:

1. Apparatus for directly measuring the quatity $\sqrt{\rho c k}$ of a test specimen where $\rho$ is the density, $c$ is the specific heat and $k$ is the thermal conductivity of the specimen comprising:

a reference specimen;

a heat source;

means for simultaneously subjecting said test specimen and said reference specimen to said heat source;

means attached to said reference specimen for producing a first electrical analog signal proportional to the heating rate $\dot{Q}$ that said test specimen is subjected to;

infrared radiometer means aimed at said test specimen for producing a second electrical analog signal proportional to the surface temperature T of said specimen; and computer means receiving said first and second analog signals for calculating $\sqrt{\rho c k}$ in accordance with the equation:

$$\sqrt{\rho c k} = \frac{\dot{Q}}{T - T_i} \frac{2}{\sqrt{\pi}} \sqrt{t}$$

where $T_i$ is the initial test specimen temperature and $t$ is the elapsed time from the time that the specimens are subjected to the heat source.

2. Apparatus according to the claim 1 wherein said means for simultaneously subjecting said test specimen and said reference specimen to said heat source includes a water-cooled shutter that shield the test and reference specimens from the heat source until the shutter is moved.

3. Apparatus according to claim 1 including a water-absorption filter located between the heat source and said specimen to filter off radiation with wavelengths of about 1.8 microns and above.

4. Apparatus according to claim 3 wherein said water-absorption filter is two plates of glass with running water inbetween.

5. Apparatus according to claim 1 including a microswitch attached to said shutter for applying a signal to said computer the instant the specimens are subjected to the heat source.

6. Apparatus according to claim 1 wherein said computer means includes an analog-to-digital converter for converting said first end second analog signals to digital signals and a digital computer receiving the digital signals.

7. Apparatus according to claim 1 including a teleprinter means for printing the results of the tests in terms of $\sqrt{\rho c k}$, time, and Q immediately after completion of a test.

* * * * *